(12) United States Patent
Snow

(10) Patent No.: US 8,734,480 B2
(45) Date of Patent: May 27, 2014

(54) VASCULAR FILTER

(75) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 175 days.

(21) Appl. No.: 13/204,462

(22) Filed: Aug. 5, 2011

(65) Prior Publication Data

US 2013/0035713 A1    Feb. 7, 2013

(51) Int. Cl.
*A61M 29/00* (2006.01)

(52) U.S. Cl.
USPC .......................................... 606/200

(58) Field of Classification Search
USPC .......................... 606/198, 159, 200
See application file for complete search history.

(56) References Cited

U.S. PATENT DOCUMENTS

| | | | |
|---|---|---|---|
| 4,132,650 A | 1/1979 | Krisch et al. | |
| 4,494,531 A | 1/1985 | Gianturco | |
| 4,619,246 A | 10/1986 | Molgaard-Nielsen | |
| 4,781,177 A | 11/1988 | Lebigot | |
| 4,832,055 A | 5/1989 | Palestrant | |
| 4,900,312 A | 2/1990 | Nadeau | |
| 5,133,733 A | 7/1992 | Rasmussen et al. | |
| 5,234,458 A | 8/1993 | Metais | |
| 5,242,462 A | 9/1993 | El-Nounou et al. | |
| 5,312,479 A | 5/1994 | Weinstein et al. | |
| 5,324,304 A | 6/1994 | Rasmussen | |
| 5,334,458 A * | 8/1994 | Powers et al. | 428/517 |
| 5,370,657 A | 12/1994 | Irie | |
| 5,375,612 A | 12/1994 | Cottenceau et al. | |
| 5,437,655 A | 8/1995 | Bartholomew | |
| 5,484,474 A | 1/1996 | Weinstein et al. | |
| 5,601,568 A | 2/1997 | Chevillon et al. | |
| 5,626,605 A | 5/1997 | Irie | |
| 5,634,942 A | 6/1997 | Chevillon et al. | |
| 5,669,933 A | 9/1997 | Simon | |
| 5,709,704 A | 1/1998 | Nott et al. | |
| 5,795,322 A | 8/1998 | Boudewijn | |
| 5,810,874 A | 9/1998 | Lefebvre | |
| 5,836,968 A | 11/1998 | Simon et al. | |
| 5,836,969 A | 11/1998 | Kim | |
| 5,853,420 A | 12/1998 | Chevillon et al. | |
| 5,879,381 A | 3/1999 | Moriuchi | |
| 5,954,741 A | 9/1999 | Fox | |
| 5,976,172 A | 11/1999 | Homsma et al. | |
| 5,984,947 A | 11/1999 | Smith | |
| 6,007,558 A | 12/1999 | Ravenscroft et al. | |

(Continued)

FOREIGN PATENT DOCUMENTS

WO    WO2010091118    8/2010

OTHER PUBLICATIONS

Office Action dated Sep. 26, 2012 for U.S. Appl. No. 12/722,484.

(Continued)

*Primary Examiner* — Tuan V Nguyen
(74) *Attorney, Agent, or Firm* — Stoel Rives LLP

(57) ABSTRACT

A filter, configured to be disposed within a body lumen, that includes one or more filtering zones. The filter may include one or more sets of legs, configured to interact with the body lumen wall in order to stabilize the position of the filter and to create a filtering structure. In some embodiments the filter may be integrally formed form a single tube of material.

47 Claims, 9 Drawing Sheets

(56) References Cited

U.S. PATENT DOCUMENTS

| | | | |
|---|---|---|---|
| 6,013,093 A | 1/2000 | Nott et al. | |
| 6,059,825 A | 5/2000 | Hobbs | |
| 6,099,549 A | 8/2000 | Bosma et al. | |
| 6,117,165 A | 9/2000 | Becker | |
| 6,156,055 A | 12/2000 | Ravenscroft | |
| 6,193,739 B1 | 2/2001 | Chevillon et al. | |
| 6,214,025 B1 | 4/2001 | Thistle et al. | |
| 6,241,746 B1 | 6/2001 | Bosma et al. | |
| 6,258,026 B1 | 7/2001 | Ravenscroft et al. | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,306,141 B1 | 10/2001 | Jervis | |
| 6,328,719 B1 | 12/2001 | Holtermann et al. | |
| 6,347,711 B1 | 2/2002 | Goebel et al. | |
| 6,391,045 B1 | 5/2002 | Kim | |
| 6,428,559 B1 | 8/2002 | Johnson | |
| 6,436,121 B1 | 8/2002 | Blom | |
| 6,443,972 B1 | 9/2002 | Bosma | |
| 6,461,370 B1 | 10/2002 | Gray et al. | |
| 6,468,290 B1 | 10/2002 | Weldon et al. | |
| 6,485,501 B1 | 11/2002 | Green | |
| 6,506,205 B2 | 1/2003 | Goldberg et al. | |
| 6,511,496 B1 | 1/2003 | Huter et al. | |
| 6,527,962 B1 | 3/2003 | Nadal | |
| 6,540,722 B1 | 4/2003 | Boyle et al. | |
| 6,540,768 B1 | 4/2003 | Diaz et al. | |
| 6,589,266 B2 | 7/2003 | Whitcher et al. | |
| 6,596,011 B2 | 7/2003 | Johnson et al. | |
| 6,620,183 B2 | 9/2003 | DiMatteo | |
| 6,623,506 B2 | 9/2003 | McGuckin, Jr. et al. | |
| 6,656,203 B2 | 12/2003 | Roth et al. | |
| 6,660,021 B1 | 12/2003 | Palmer et al. | |
| 6,726,701 B2 | 4/2004 | Gilson | |
| 6,783,538 B2 | 8/2004 | McGuckin, Jr. et al. | |
| 6,793,665 B2 | 9/2004 | McGuckin, Jr. et al. | |
| 6,932,831 B2 | 8/2005 | Forber | |
| 6,939,361 B1 | 9/2005 | Kleshinski | |
| 6,958,074 B2 | 10/2005 | Russell | |
| 6,989,021 B2 | 1/2006 | Bosma | |
| 6,991,641 B2 | 1/2006 | Diaz et al. | |
| 7,147,649 B2 | 12/2006 | Thomas | |
| 7,179,275 B2 | 2/2007 | McGuckin, Jr. | |
| 7,261,731 B2 | 8/2007 | Patel | |
| 7,279,000 B2 | 10/2007 | Cartier et al. | |
| 7,314,477 B1 | 1/2008 | Ravenscroft et al. | |
| 7,323,002 B2 | 1/2008 | Johnson et al. | |
| 7,329,227 B2 | 2/2008 | Schramm | |
| 7,329,269 B2 | 2/2008 | Shapiro et al. | |
| 7,338,512 B2 | 3/2008 | McGuckin, Jr. et al. | |
| 7,344,549 B2 | 3/2008 | Boyle et al. | |
| 7,399,308 B2 | 7/2008 | Borillo et al. | |
| 7,534,251 B2 | 5/2009 | WasDyke | |
| 7,544,202 B2 | 6/2009 | Cartier et al. | |
| 7,582,100 B2 | 9/2009 | Johnson | |
| 7,625,390 B2 | 12/2009 | Hendriksen et al. | |
| 7,699,865 B2 | 4/2010 | Johnson et al. | |
| 7,699,867 B2 | 4/2010 | Hendriksen et al. | |
| 7,704,266 B2 | 4/2010 | Thinnes, Jr. et al. | |
| 7,704,267 B2 | 4/2010 | Tessmer | |
| 7,736,383 B2 | 6/2010 | Bressler et al. | |
| 7,749,246 B2 | 7/2010 | McGuckin et al. | |
| 7,763,045 B2 | 7/2010 | Osborne | |
| 7,771,452 B2 | 8/2010 | Pal et al. | |
| 7,780,694 B2 | 8/2010 | Palmer et al. | |
| 7,794,473 B2 | 9/2010 | Tessmer et al. | |
| 7,803,171 B1 | 9/2010 | Uflacker | |
| 7,862,577 B2 | 1/2011 | Gray et al. | |
| 7,887,561 B2 | 2/2011 | McGuckin, Jr. et al. | |
| 7,909,847 B2 | 3/2011 | McGuckin, Jr. et al. | |
| 7,931,664 B2 | 4/2011 | Gray et al. | |
| 7,959,647 B2 | 6/2011 | Palmer | |
| 7,967,838 B2 | 6/2011 | Chanduszko et al. | |
| 7,972,353 B2 | 7/2011 | Hendriksen et al. | |
| 7,976,562 B2 | 7/2011 | Bressler et al. | |
| 7,996,993 B2 | 8/2011 | Gray et al. | |
| 8,025,675 B2 | 9/2011 | Shirley et al. | |
| 8,029,529 B1 | 10/2011 | Chankduszko | |
| 8,043,322 B2 | 10/2011 | Hendriksen et al. | |
| 8,057,506 B2 | 11/2011 | Gilson et al. | |
| 8,057,507 B2 | 11/2011 | Horan et al. | |
| 8,062,326 B2 | 11/2011 | McGuckin, Jr. et al. | |
| 8,062,327 B2 | 11/2011 | Chanduszko et al. | |
| 8,062,328 B2 | 11/2011 | Hallisey | |
| 8,092,484 B2 | 1/2012 | Kashkarov et al. | |
| 8,092,485 B2 | 1/2012 | Lapid | |
| 8,100,936 B2 | 1/2012 | McGuckin, Jr. et al. | |
| 8,105,349 B2 | 1/2012 | Hendriksen et al. | |
| 8,118,828 B2 | 2/2012 | Cartier et al. | |
| 8,133,251 B2 | 3/2012 | Ravenscroft et al. | |
| 8,133,252 B2 | 3/2012 | Davis et al. | |
| 8,162,972 B2 | 4/2012 | McGuckin, Jr. et al. | |
| 8,167,901 B2 | 5/2012 | Hendriksen et al. | |
| 8,211,140 B2 | 7/2012 | McGunkin, Jr. et al. | |
| 8,246,648 B2 | 8/2012 | Tekulve | |
| 8,246,650 B2 | 8/2012 | Osborne | |
| 8,246,651 B2 | 8/2012 | Hendriksen et al. | |
| 8,252,017 B2 | 8/2012 | Paul, Jr. et al. | |
| 8,252,019 B2 | 8/2012 | Fleming, III | |
| 8,267,954 B2 | 9/2012 | Decant, Jr. et al. | |
| 8,282,668 B2 * | 10/2012 | McGuckin et al. | 606/200 |
| 8,317,818 B2 | 11/2012 | Kashkarov et al. | |
| 8,333,785 B2 | 12/2012 | Chanduszko et al. | |
| 8,353,926 B2 | 1/2013 | Silver | |
| 8,366,736 B2 | 2/2013 | Thinnes, Jr. et al. | |
| 8,383,926 B2 | 2/2013 | Plissonnier et al. | |
| 2001/0000799 A1 | 5/2001 | Wessman | |
| 2001/0039432 A1 | 11/2001 | Whitcher et al. | |
| 2002/0058911 A1 | 5/2002 | Gilson et al. | |
| 2002/0062134 A1 | 5/2002 | Barbut et al. | |
| 2002/0111647 A1 | 8/2002 | Khairkhahan et al. | |
| 2003/0109897 A1 | 6/2003 | Walak et al. | |
| 2004/0116959 A1 | 6/2004 | McGuckin | |
| 2004/0220610 A1 | 11/2004 | Kriedler et al. | |
| 2005/0004596 A1 | 1/2005 | McGuckin, Jr. et al. | |
| 2005/0015111 A1 * | 1/2005 | McGuckin et al. | 606/200 |
| 2005/0080447 A1 | 4/2005 | McCuckin, Jr. et al. | |
| 2005/0222604 A1 | 10/2005 | Shaeffer | |
| 2005/0267515 A1 | 12/2005 | Oliva et al. | |
| 2005/0288704 A1 | 12/2005 | Cartier | |
| 2005/0288705 A1 | 12/2005 | Gilson | |
| 2006/0009799 A1 | 1/2006 | Kleshinski | |
| 2006/0041271 A1 | 2/2006 | Bosma et al. | |
| 2006/0079928 A1 | 4/2006 | Cartier | |
| 2006/0079930 A1 | 4/2006 | McGuckin | |
| 2006/0100659 A1 | 5/2006 | Dinh et al. | |
| 2006/0106417 A1 | 5/2006 | Tessmer | |
| 2006/0206138 A1 | 9/2006 | Eidenschink | |
| 2007/0005095 A1 | 1/2007 | Osborne | |
| 2007/0141107 A1 | 6/2007 | Kutryk | |
| 2007/0162048 A1 | 7/2007 | Quinn et al. | |
| 2007/0167974 A1 | 7/2007 | Cully | |
| 2007/0173885 A1 | 7/2007 | Cartier | |
| 2007/0191932 A1 | 8/2007 | Kutryk | |
| 2007/0198050 A1 | 8/2007 | Ravenscroft | |
| 2008/0027481 A1 | 1/2008 | Gilson | |
| 2008/0033479 A1 | 2/2008 | Silver | |
| 2008/0097518 A1 | 4/2008 | Thinnes | |
| 2008/0234722 A1 | 9/2008 | Bonnette et al. | |
| 2008/0275487 A1 | 11/2008 | Fleming | |
| 2008/0275492 A1 | 11/2008 | Farmiga | |
| 2009/0043332 A1 | 2/2009 | Sullivan et al. | |
| 2009/0069840 A1 | 3/2009 | Halllisey | |
| 2009/0198270 A1 | 8/2009 | McGuckin, Jr. et al. | |
| 2009/0254117 A1 | 10/2009 | Pakter | |
| 2009/0299403 A1 | 12/2009 | Chanduszko et al. | |
| 2009/0299404 A1 | 12/2009 | Chanduszko | |
| 2010/0049238 A1 | 2/2010 | Simpson | |
| 2010/0174310 A1 | 7/2010 | Tessmer | |
| 2010/0185229 A1 | 7/2010 | Horan et al. | |
| 2010/0185230 A1 | 7/2010 | Horan et al. | |
| 2010/0198252 A1 | 8/2010 | Beyer et al. | |
| 2010/0318115 A1 | 12/2010 | Chanduszko et al. | |
| 2011/0040321 A1 | 2/2011 | Cartier | |

(56) References Cited

U.S. PATENT DOCUMENTS

| | | |
|---|---|---|
| 2011/0106133 A1 | 5/2011 | O'Connell et al. |
| 2011/0137335 A1 | 6/2011 | Hallisey |
| 2011/0166593 A1 | 7/2011 | Paul, Jr. |
| 2011/0202086 A1 | 8/2011 | Bates |
| 2011/0208233 A1 | 8/2011 | McGuckin, Jr. et al. |
| 2012/0089173 A1 | 4/2012 | Tukulve |
| 2012/0109181 A1 | 5/2012 | Hallisey |
| 2012/0130418 A1 | 5/2012 | Jenson et al. |
| 2012/0184985 A1 | 7/2012 | Ravenscroft et al. |
| 2012/0245622 A1 | 9/2012 | McGuckin, Jr. et al. |
| 2013/0018387 A1 | 1/2013 | Diamant |
| 2013/0035714 A1 | 2/2013 | Snow |

OTHER PUBLICATIONS

International Search Report and Written Opinion dated Jan. 30, 2013 for PCT/US2012/047004.
International Search Report and Written Opinion dated Jan. 30, 2013 for PCT/US2012/047023.
Restriction Requirement dated Nov. 21, 2011 for U.S. Appl. No. 12/722,484.
Office Action dated Mar. 6, 2012 for U.S. Appl. No. 12/722,484.
International Search and Written Opinion dated Jun. 13, 2013 for PCT/US2013/027427.
U.S. Appl. No. 13/204,462, filed Aug. 5, 2011, Snow.
Boothroyd et al., 'Product Design for Manufacture and Assembly.' 1994, p. 64.
International Preliminary Report for Application No. PCT/US08/75102 dated Mar. 9, 2010.
International Publication and Written Opinion for Application No. PCT/US08/75102 dated Mar. 12, 2009.
Cipolla et al., 'Complications of Vena Cava Filters: A Comprehensive Clinical Review.' OPUS 12 Scientist 2008; vol. 2, No. 2: 11-24.
Katsamouris et al. 'Inferior Vena Cava Filters: In Vitro Comparison of Clot Trapping and Flow Dynamics.' Radiology 1988; 166:361-366.
Prince et al., 'The diameter of the inferior Vena Cava and It's Implications for the Use of Vena Caval Filters.' Radiology 1983; 149:687-689.
Simon et al., 'Comparative Evaluation of Clinically Available Inferior Vena Cava Filters with an In Vitro Physiologic Simulation of the Vena Cava.' Radiology 1993; 189:769-774.
Lorch et al., 'In Vitro Studies of Temporary Vena Cava Filters.' CardioVascular and Interventional Radiology 1998; 21:146-150.
Neuerburg et al., 'New Retrievable Percutaneous Vena Cava Filter: Experimental In Vitro and In Vivo Evaluation.' CardioVascular and Interventional Radiology 1993: 16:224-229.
Reekers et al., 'Evaluation of the Retrievability of the OptEase IVC Filter in an Animal Model.' J Vasc Interv Radiol 2004; 15:261-267.
Kinney, 'Update on Inferior Vena Cava Filters.' J Vasc Interv Radiol 2003; 14:425-440.
Bruckheimer et al., 'In Vitro Evaluation of a Retrievable Low-Profile Nitinol Vena Cava Filter.' J Vasc Interv Radiol 2003; 14:469-474.
Brountzos et al., 'A New Optional Vena Cava Filter: Retrieval at 12 Weeks in an Animal Model.' J Vasc Interv Radiol 2003; 14:763-772.
Ray et al., 'Outcomes with Retrievable Inferior Vena Cava Filters: A Multicenter Study.' J Vasc Interv Radiol 2006; 17:1595-1604.
Kaufman et al., 'Guidelines for the Use of Retrievable and Convertible Vena Cava Filters: Report from the Society of Interventional Radiology Mulitdisciplinary consensus conference.' J Vasc Interv Radiol 2006; 17:449-459.
Kolbeck et al., 'Optional Inferior Vena Cava Filter Retrieval with Retained Thrombus: An In Vitro Model.' J Vasc Interv Radiol 2006; 17:685-691.
Lorch et al., 'Current Practice of Temporary Vena Cava Filter Insertion: A Multicenter Registry.' JVIR 2000; 11:83-88.
Rousseau et al., 'The 6-F Nitinol TrapEase Inferior Vena Cava Filter: Results of a Prospective Multicenter Trial.' J Vasc Interv Radiol 2001; 12:299-304.
Stoneham et al., 'Temporary Inferior Vena Cava Filters: In Vitro Comparison with Permanent IVC Filters.' JVIR 1995; 6:731-736.
Crochet et al., 'Evaluation of the LGM Vena Cava-Tech Infrarenal Vena Cava Filter in and Ovine Venous Thromboembolism Model.' J Vasc Interv Radiol 2001; 12:739-745.
Kaufman, 'Guidelines for the Use of Optional Retrievable Vena Cava Filters.' European Respiratory Disease 2007; 31-34.
Epstein et al., 'Experience with the Amplatz Retrievable Vena Cava Filter.' Radiology 1989; 172:105-110.
Inferior Vena Cava Filter, ISI Interventional & Surgical Innovations LLC. Product Brochure, Copyright 2008.
The Clot Stopper (online) Retrieved from the internet URL:http://www.americanheritage.com/people/articles/web/20060715-pulmonary-embolism-blood-clot-lazar-greenfield-gamnan-kimmel-surgery-medical-doctor-surgeon. shtml Summer 2006, vol. 22 Issue 1.
Simon Nitinol Filter, Versatile and Dependable Performance. Bard Peripheral Vascular (online) Retrieved from the internet URL:http://www.bardpv.com_vascular/product.php?p=23 Copyright 2004.
Aegisy Vena Cava Filter. Shenzhen Lifetech Scientific Inc. (online). Retrieved from the internet URL:http://www.lifetechmed.com/english/product/product6.htm Copyright 2005.
Safe Flo Vena Cava Filter (online)m Retrieved from the internet <URL:www.rafaelmedical.com>.
Aegisy Vena Cava Filter Product Description (online) Retrieved from the internet URL:http://www.lifetechclinic.com/upload/article/vena/instruction_for_use.htm Accessed Jun. 6, 2008.
Design History (online). Retrieved from the internet URL:http://www.lifetechclinic.com/upload/article/vena/vena_cava_filter.htm Accessed Jun. 6, 2008.
Crux Biomedical, Inc. Inferior Vena Cava Filter System Instructions for Use, IFU P/N 0001 Rev.B, DCO# 0027, Effective Date Feb. 2, 2007.
Smouse, 'Next Generation Filters: Are There Improvements Over the Existing Filters?', Powerpoint Presentation. University of Illinois College of Medicine at Peoria.
Kaufman, 'Vena Cava Filters as a Risk Factor for VTE'. Powerpoint Presentation at the SIR Foundation Jun. 2007 IVC Filter Research Consensus Panel.
Rectenwald, 'Are All IVC's the Same.' Powerpoint Presentation at the SIR Foundation Jun. 2007 IVC Filter Research Consensus Panel.
Rogers, 'Vena Cava Filter Outcomes.' Powerpoint Presentation at the SIR Foundation Jun. 2007 IVC Filter Research Consensus Panel.
SIR Foundation Research Consensus Panel for the Development of a Research Agenda in Inferior Vena Cava Filters, Jun. 12, 2007—Herndon, VA. Powerpoint Presentation at the SIR Foundation Jun. 2007 IVC Filter Research Consensus Panel.
TrapEase Vena Cava Filter User's Instruction. Cordis Corp, 2008.
Corriere et al., 'Vena Cava Filters: An Update.' Future Cardiol 2006: 2(6): 695-707.
Mohan, C. et al. 'Comparative Efficacy and Complications of Vena Caval Filters.' J Vasc Surg 1995; 21:235-246.
Linsenmaier, U. et al., 'Indications, Management, and Complications of Temporary Inferior Vena Cava Filters.' Cardiovascular Intervent, Radiol 1998; 21(6): 464-469.
Asch et al. Radiology 2002; 29:173-176.
Cunliffe et al., 'A Fatal Complication of a Vena Cava Filter Associated with Pulmonary Thromboembolism.' Am J Forensic Med Pathol 2008; 29:173-176.
Joels et al., 'Complications of Inferior Vena Cava Filters.' Am Surg 2003; 69:654-659.
Pulmonary Embolism (online). Retrieved from internet URL:http//www.mayoclinic.com/health/pulmonary-embolism/DS00429/DSECTION=complications By Mayo Clinic Staff Sep. 28, 2007.
Cordis TrapEase Permanent Vena Cava Filter with the VisEase Angiographic Vessel Dilator (on line). Retrieved from <URL:http//www.mitek.com/home.jhtml?loc=USENG&page=viewcontent&contentid=09008b9880ffdcbf&nodekey=1Prod_Info/Type/Endovascular_Disease_Management/Vena_Cava_Filters&parentid=fc0de00100001215> 2000-2008.
Decousus et al., 'A Clinical Trial of Vena Caval Filters in the Prevention of Pulmonary Embolism in Patients with Proximal Deep-Vein Thrombosis.' The New England Journal of Medicine, Feb. 12, 1998; vol. 338, No. 7.
Notice of Allowance for U.S. Appl. No. 12/203,515 dated Jul. 13, 2011.
Office Action dated Mar. 29, 2013 for U.S. Appl. No. 13/204,492.
U.S. Appl. No. 13/774,598, filed Feb. 22, 2013, Snow.

* cited by examiner

VASCULAR FILTER

TECHNICAL FIELD

The present disclosure relates generally to filters configured to be disposed within a body lumen. More particularly, the present disclosure relates to filters or similar devices that may be configured to capture blood clots within the vasculature, such as within the inferior vena cava.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a detail view, taken through line 1A-1A, of a portion of the filter of FIG. 1.

DETAILED DESCRIPTION

A filter may be configured to be disposed within the vasculature to capture or trap material within a body lumen. For example, a filter may be configured to trap blood clots in the vasculature. In some embodiments, a filter may be disposed within the inferior vena cava and be configured to inhibit pulmonary embolism. Furthermore, a filter may be configured to be removable.

Though many of the examples provided herein may refer to a filter disposed within the inferior vena cava, the present disclosure is applicable to a variety of filters configured to be disposed elsewhere within the vasculature or within other body lumens.

It will be readily understood that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner while the practitioner is placing or manipulating the device, while the distal end is the opposite end. For example, the proximal end of a filter refers to the end nearest the practitioner when the filter is disposed within, or being deployed from, a deployment device. For consistency throughout, these terms remain constant in the case of a deployed filter, regardless of the orientation of the filter within the body.

Figure 1:
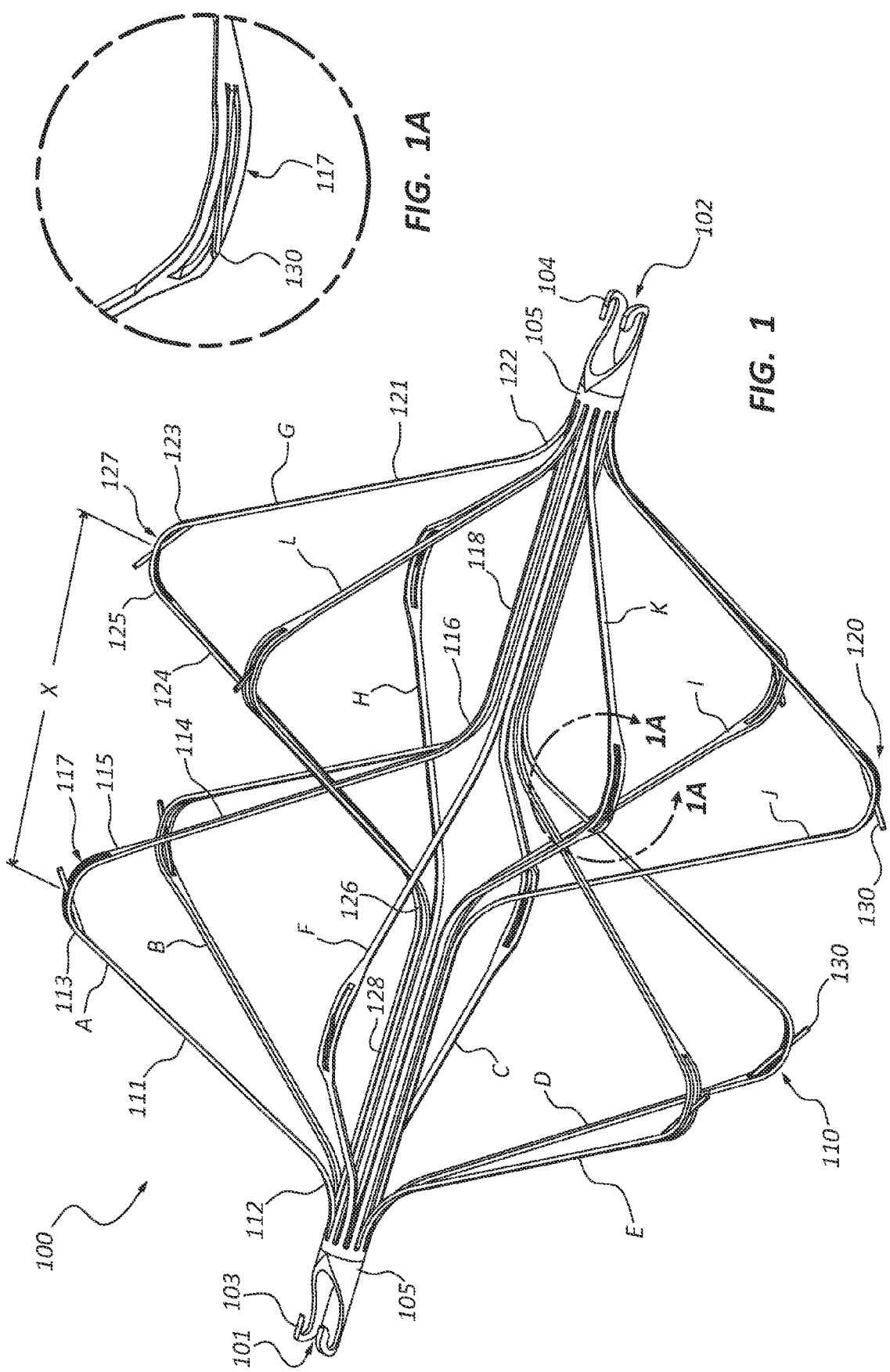
FIG. 1 is a perspective view of a filter.

FIG. 1 is a perspective view of a filter 100. The filter 100 of FIG. 1 comprises an axial member, such as the central tubular portion 105 coupled to multiple legs 110, 120. In this embodiment, the tubular portion 105 may be understood as a central structural component that ties the other components together. Moreover, the tubular portion 105 of FIG. 1 may also be understood to define a tubular surface running along the central axis of the filter. In the embodiment of FIG. 1, the tubular portion 105 includes the two circumferential rings at each end of the filter (the portions marked 105 in FIG. 1) and the tubular surface is a hypothetical surface extending between the rings. This tubular surface is not a component of the filter 100, but rather is an imaginary surface defining a central portion of the filter 100, referenced here for convenience in describing the structure of the filter. For example, in the embodiment of FIG. 1, portions of the legs—for example, portions 118 and 128, discussed later—may be described as lying on the tubular surface of the filter 100. Thus, as used herein, the tubular portion 105 refers to the structural tubular components of the filter 100 while the tubular surface refers to an imaginary surface extending between the tubular portions.

Furthermore, the tubular portion 105 and the tubular surface may be used to define a central axis of the filter 100. The "axis" of the filter, as used herein, refers to the longitudinal centerline of the filter; this axis corresponding to the longitudinal axis of the tubular surface. Some embodiments may not include tubular portions such as portion 105 or have a readily identifiable tubular surface. In such embodiments, the center axis of the filter may still be understood as a line through the center of the filter. In some embodiments, the filter may be configured such that the center axis of the filter is designed to be disposed substantially along the center axis of a lumen in which the filter is deployed.

In the following description, components of the filter 100 may therefore be described with reference to the tubular portion 105, the tubular surface, and/or the axis of the filter. (That is, a component may be described as extending radially outward from the axis of the tubular surface, or positioned along the longitudinal direction of the tubular surface, for example.) Again, notwithstanding this method of description, other embodiments within the scope of this disclosure may or may not include an identifiable tubular portion such as portion 105. Disclosure provided in connection with components of filters having tubular portions is applicable to analogous or substantially analogous components of filters without tubular portions.

In the embodiment of FIG. 1, tubular portion 105 is coupled to a proximal hook 103 adjacent the proximal end 101 of the filter 100 and a distal hook 104 adjacent the distal end 102 of the filter. In some embodiments, one or both of the proximal hook 103 and the distal hook 104 may be used in retrieving or repositioning the filter 100. In other embodiments, a filter may include only one hook at either the proximal 101 or distal 102 end of the filter 100.

Filter 100 also includes a first set of legs 110, which includes six legs (A, B, C, D, E, and F) in the illustrated embodiment. In other embodiments the first set of legs 110 may consist of more or fewer legs, for example, from three to nine legs or from five to seven legs, specifically three, four, five, seven, eight, or nine legs. Likewise, while in the embodiment of FIG. 1 each leg of the first set of legs 110 has substantially the same shape as the other legs of the first set of legs 110, in other embodiments legs within a set of legs may have differing shapes. Further, though in the embodiment of FIG. 1 the legs of the first set of legs are substantially evenly spaced around the center axis of the filter 100, in other embodiments the legs may be irregularly spaced.

In the illustrated embodiment, the legs A, B, C, D, E, F of the first set of legs 110 are substantially identical in size and shape. Thus, disclosure provided in connection with one leg is equally applicable to the other legs. Specifically, certain features of the first set of legs 110 are disclosed below in connection with leg A. This disclosure is equally applicable to legs B, C, D, E, and F. Furthermore, reference numerals shown in the Figures in connection with one leg may be used to refer to the analogous component or portion of another leg, though for clarity in the drawings, each component of each leg is not labeled.

Leg A of the first set of legs 110 of the filter 100 of FIG. 1 may comprise a first portion 111, a second portion 114, and a transition portion 118. The first portion 111 may have an inner segment 112 coupled to the tubular portion 105 of the filter 100 and an outer segment 113 coupled to the second portion 114 of leg A. The second portion 114 may have an outer segment 115 coupled to the first portion 111 and an inner segment 116 coupled to the transition portion 118. In the illustrated embodiment, the first portion 111 and the second portion 114 are coupled to each other at an apex 117. The inside surfaces of the first portion 111 and the second portion 114 define and acute angle. The external angle between the outside surface of the first portion 11 and the tubular portion 105 define an obtuse angle. As explained above, because each leg of the first set of legs 110 is identical to the others, the reference numerals used in connection with leg A are also applicable to the components of the other legs. For example, though 117 is used above to refer to the apex of leg A specifically, 117 can also be used to indicate the other apexes of the first set of legs 110 as well.

Leg A may be configured such that the first portion 111, from the inner segment 112 to the outer segment 113, extends radially outward from the axis of the filter 100. Analogously, the second portion 114, from the outer segment 115 to the inner segment 116, may extend radially inward toward the axis of the filter 100. Further, the transition portion 118 may couple the second portion 114 to the tubular portion 105. In certain embodiments, including the one illustrated, the transition portion 118 is disposed substantially parallel to the axis of the filter 100. In other embodiments the transition portion 118 may be relatively longer or shorter than shown in the illustrated embodiment, including embodiments where there is no transition section at all and the second portion 114 couples directly to the tubular portion 105. Furthermore, the transition section 118 need not be parallel to the axis of the filter 100, for example, it may be disposed radially outward from the tubular surface, including embodiments where the transition section is closer to the axis of the filter 100 near the tubular portion 105 than it is near the second portion 114. Regardless of whether the legs of the filter include a transition portion, in some embodiments portions of the legs which are curved may be comprised of curves having a generally sinusoidal configuration, for example, smooth curves.

The filter 100 may be configured such that the apexes 117 of each leg of the first set of legs 110 are sufficiently displaced from the center axis of the filter 100 that the apexes 117 contact the lumen wall when the filter 100 is disposed within such a lumen.

The filter 100 of FIG. 1 also comprises a second set of legs 120, including legs G, H, I, J, K, and L. Like the first set of legs 110, in other embodiments the second set of legs 120 may include more or fewer than six legs, for example from three to nine legs or from five to seven legs. Furthermore, in some embodiments a filter may be configured with a different number of legs in the first set of legs 110 than in the second set of legs 120.

The legs of the second set of legs 120 of the embodiment of FIG. 1 are substantially identical to the legs of the first set of legs 110, but located at a different position along the tubular surface. Thus, the disclosure provided in connection with the first set of legs 110 is equally applicable to the second set of legs 120 and vice versa. For example, leg G of the second set of legs comprises a first portion 121, having an inner segment 122 and an outer segment 123, a second portion 124 having an outer segment 125 and an inner segment 126, a transition portion 128, and an apex 127. These components are analogous to the similarly named components of the first set of legs 110. Further, each leg of the second set of legs 120 is, in certain embodiments, substantially identical to the others, thus disclosure applicable to leg G is equally applicable to the other legs of the second set of legs 120. As with the first set of legs 110, in other embodiments the second set of legs 120 may include legs that are not identical in size, shape, or position.

In the embodiment of FIG. 1, the apexes 117 of the first set of legs 110 are each located at substantially the same longitudinal position along the axis of the filter 100. Similarly, the apexes 127 of the second set of legs 120 are also located in substantially the same longitudinal position along the filter axis as each other. In some embodiments the apexes 117 of the first set of legs 110 may be displaced a distance along the longitudinal axis of the filter 100 from the apexes 127 of the second set of legs 120. In the illustrated embodiment, this displacement is labeled as distance "X." In some embodiments, distance X may be configured to maintain the position of a filter substantially in the center of a body lumen. For example, in some instances, a relatively greater distance, X, between the two sets of apexes 117, 127 may increase the stability of the filter within the lumen and minimize the degree to which the filter can rotate out of axial alignment with the lumen. In some embodiments distance X may be from about 0.200 inches to about 1.000 inches.

The first set of legs 110 and the second set of legs 120 may be configured to filter fluid flowing past the filter 100. In some embodiments, portions of the legs 110, 120 may be configured to define radially expanding filtering surfaces, such as frustoconical surfaces. For example, the filter 100 of FIG. 1 may be described as having at least four filtering zones, a zone corresponding to each of four radially expanding surfaces: (1) a frustoconical surface defined by the first portions 111 of the first set of legs 110; (2) a frustoconical surface defined by the second portions 114 of the first set of legs 110; (3) a frustoconical surface defined by the first portions 121 of the second set of legs 120; and (4) a frustoconical surface defined by the second portions 124 of the second set of legs 120. A clot or other object disposed within a fluid stream would necessarily have to pass each of these zones in order to pass a filter disposed within a body lumen.

Moreover, in embodiments such as that in FIG. 1, each of the filtering zones is offset from the other filtering zones in the longitudinal direction of the filter 100. In some instances, such as instances where multiple clots are caught in different filtering zones, this may allow increased fluid flow around the clots, as compared to the potential "bottleneck" effect of multiple clots caught in a filter without longitudinally offset filtering zones.

In some embodiments, such as the embodiment of FIG. 1, each leg of the first and second sets of legs comprises a barb 130 coupled to each leg near the apex 117 of each leg. FIG. 1A is a detail view, taken through line 1A-1A of one barb 130 and apex 117. In these embodiments, the barb 130 is integrally formed from the material of the leg. Further, in such embodiments, the barb 130 is cut from a central portion of the leg, meaning the barb is formed by a generally "U-shaped" cut in the leg, which cut does not intersect the edges of the leg. In other embodiments the barb may be cut from another part of the leg or be comprised of a separate piece of material coupled to the leg. In alternative embodiments, the barb may be in the form of a spur of leg material; in these embodiments, the barb may be formed by cutting the leg only part way through, as in the barb of a fish hook. As further explained below, barbs 130 may be configured to extend into a body lumen wall, in order to minimize migration of the filter within the lumen.

Thus, according to a further embodiment of the invention, there is disclosed a device for location within a body lumen, comprising a leg and a barb 130, wherein the barb 130 may be cut from a central portion of the leg, meaning the barb is formed by a generally "U-shaped" cut in the leg, which cut may not intersect the edges of the leg.

While in the embodiment of FIG. 1, each leg of the first set of legs 110 and each leg of the second set of legs 120 is coupled to a barb 130, in other embodiments barbs may only be located on either the first set of legs 110, only the second set of legs 120, or only certain individual legs of the first 110 or second 120 sets of legs.

In the illustrated embodiment, the barbs 130 are oriented such that the barbs 130 associated with the first set of legs 110 face the opposite direction from the barbs 130 associated with the second set of legs 120. Specifically, in the illustrated embodiment, the barbs 130 associated with the first set of legs 110 are oriented such that each barb 130 extends from the leg toward to the distal end 102 of the filter 100. The barbs 130 associated with the second set of legs 120 extend toward the proximal 101 end of the filter 100. In some embodiments, filters with bi-directional barbs 130, meaning filters with some barbs oriented in opposite directions than other barbs (as described above) may be configured to prevent migration of the filter 100 in either direction along a body lumen. In other words, each barb 130 may be configured to generally prevent migration of the filter 100 in the direction the barb 130 is oriented; thus, filters with bi-directional barbs 130 may be configured to resist migration in both directions.

Figure 2:
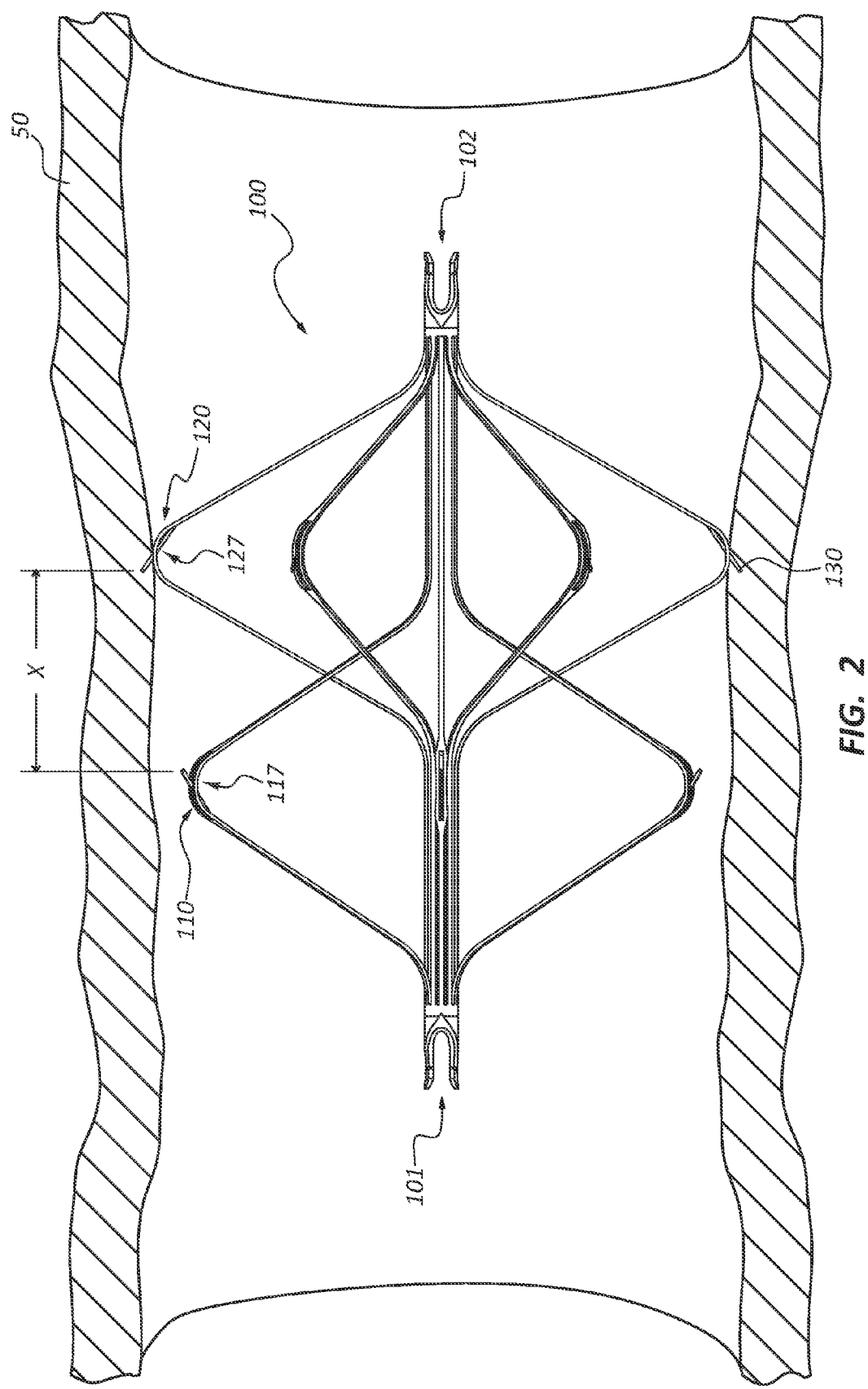
FIG. 2 is a side view of the filter of FIG. 1, disposed within a body lumen.

FIG. 2 is a side view of filter 100 disposed within a body lumen 50. In the drawing of FIG. 2, the body lumen 50 is shown as a cross section, while the filter 100 is shown in perspective. In the illustration of FIG. 2, the second set of legs 120 appears to contact the lumen 50 while the first set of legs 110 does not; this is due to the circumferential offset of the legs and the cross sectional view. Both sets of legs 110, 120 contact the lumen 50 wall in the illustrated embodiment. See also FIG. 3. The filter 100 is disposed within the body lumen 50 such that the filter 100 is substantially coaxially aligned with the body lumen 50. FIG. 2 illustrates how distance X, the longitudinal displacement of the apexes 117 of the first set of legs 110 with respect to the apexes 127 of the second set of legs 120, may affect the stability of the filter 100 in some instances. Contact between both the first set of legs 110 and the second set of legs 120 of the filter 100 and the lumen 50 may tend to keep the filter 100 centered within the body lumen 50. The displacement, X, of the two sets of legs 110, 120 may minimize the degree to which the filter 100 can pivot on the contact between either set of legs 110, 120 and the lumen 50. Thus, the migration of either the proximal 101 or distal 102 end of the filter 100 toward the body lumen 50 wall may be prevented or minimized. Accordingly, in the event that a medical practitioner wishes to remove or relocate the filter 100, the hooks 103, 104 may remain spaced from the inner wall of the body lumen 50 and be readily accessible to the practitioner. Furthermore, in some applications the tendency of the filter 100 to remain centered within the lumen 50 may maintain the relative positions and orientations of the filtering zones within the lumen 50.

FIG. 2 also illustrates how, when deployed within a body lumen 50, the barbs 130 of the filter 100 may extend into the body lumen 50 wall, further stabilizing the filter 100.

Figure 3:
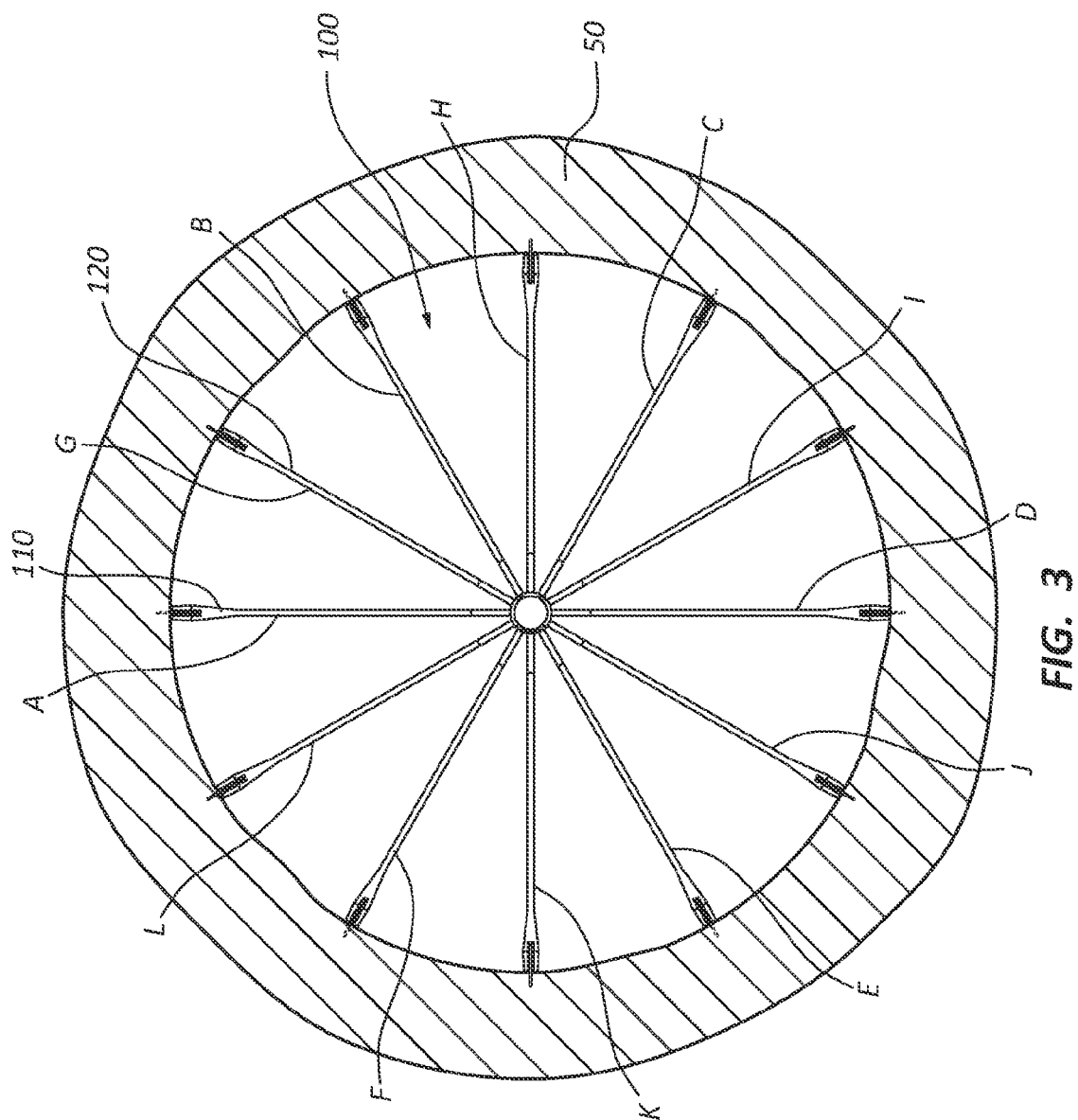
FIG. 3 is an end view of the filter of FIGS. 1 and 2, disposed within the body lumen of FIG. 2.

FIG. 3 is a front view of filter 100 disposed within a body lumen 50. As with FIG. 2, the filter 100 is not shown in cross section; instead it is shown in perspective, while the lumen 50 is shown in cross section. In the embodiment of FIG. 3, each of the legs A, B, C, D, E, F of the first set of legs 110 is evenly spaced around the center axis of the filter 100. Likewise, each of the legs G, H, I, J, K, L of the second set of legs 120 is also evenly spaced around the center axis of the filter 100. Furthermore, in the embodiment of FIG. 3, the legs of the second set of legs 120 are offset from the legs of the first set of legs 110, such that each leg of the second set of legs 120 is equally spaced between adjacent legs of the first set of legs 110 around the axis of the filter 100. In other embodiments, the first set of legs 110, the second set of legs 120, or both may not be evenly spaced or evenly offset.

Figure 4:
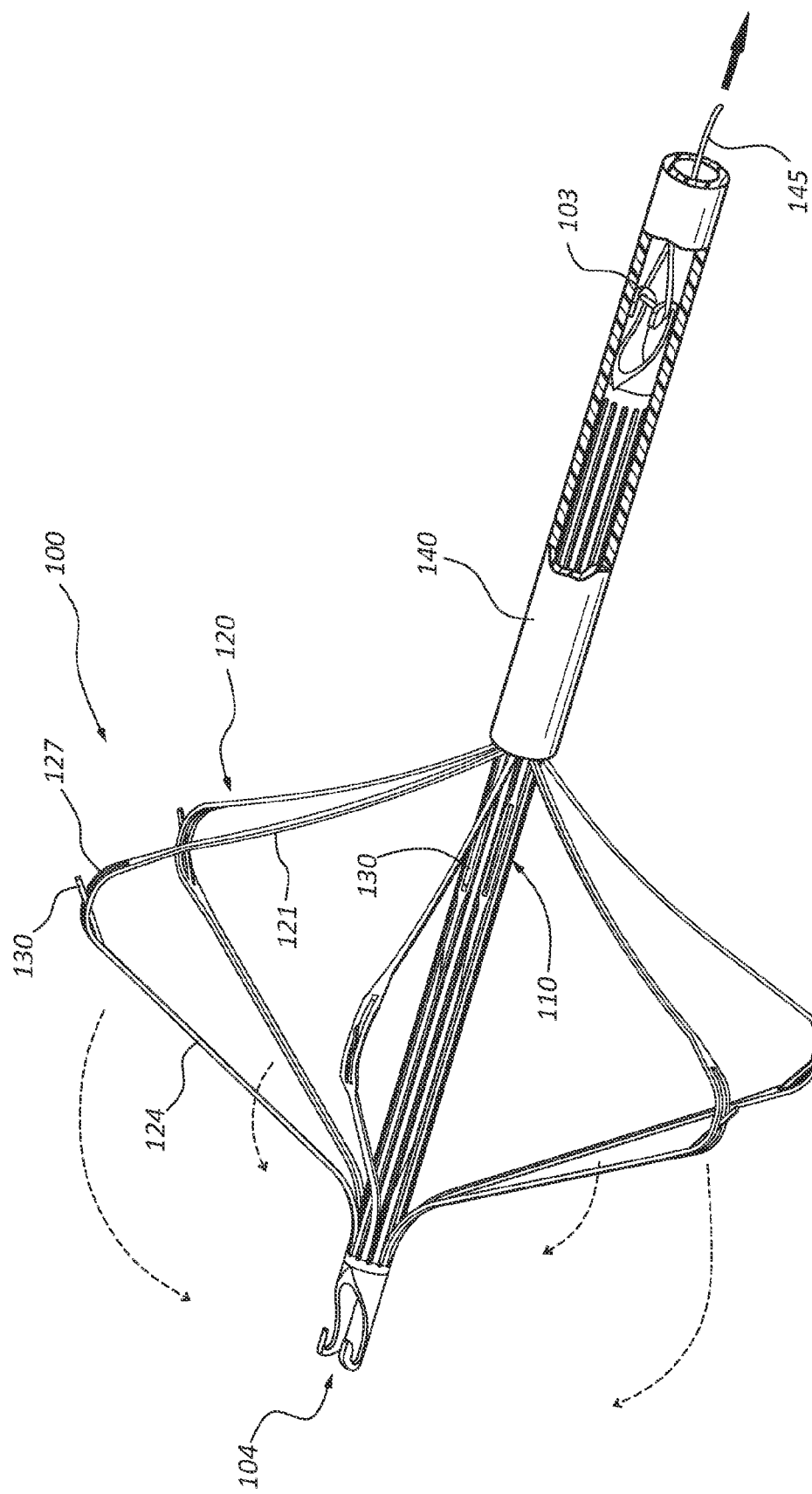
FIG. 4 is a perspective view of the filter of FIG. 1, partially disposed within a catheter.

FIG. 4 is a perspective view of filter 100, partially disposed within a catheter 140. In some instances, the legs 110, 120 may be contracted and the filter 100 disposed within a catheter 140 or other delivery/retrieval device or sheath. In some embodiments, this may be accomplished by coupling a snare 145 disposed within the catheter 140 to one of the hooks 103, 104 of the filter 100. The filter 100 may then be drawn into the catheter 140 by displacing the snare 145 with respect to the catheter 140. This displacement may bring the first set of legs 110 and the second set of legs 120 into contact with the catheter 140, thereby causing the legs to fold down as the filter 100 is drawn into the catheter 140.

In the illustrated embodiment, the filter 100 is drawn into the catheter such that the first set of legs 110 is pushed toward the center axis of the filter 100. As illustrated by the arrows, interaction of the catheter 140 with the second set of legs 120 will further cause the second set of legs 120 to fold as the filter 100 is drawn into the catheter 140. In some instances the interaction of the catheter 140 with the legs 110, 120 may cause the legs to fold such that portions of either or both sets of legs 110, 120 are disposed beyond one of the hooks 103, 104 of the filter 100 when the filter is fully inside the catheter 140. For example, as indicated by the arrows, in the embodiment of FIG. 4, portions of the second set of legs 120 will fold up beyond the distal hook 104 of the filter 100 when the filter 100 is fully within the catheter 140.

The filter 100 may be drawn into the catheter 140 in order to use the catheter 140 to place the filter 100 within a body lumen of a patient. Furthermore, the filter 100 may be partially or fully drawn back into the catheter 140 after the filter 100 is placed within the body lumen, in order to move the filter 100 within the body lumen, or to completely remove the filter 100 from the body lumen. The filter 100 may therefore be configured to be removably or permanently disposed within a body lumen of a patient.

In some embodiments, the legs 110, 120 and barbs 130 may interact such that the barbs 130 tends to become aligned with the legs 110, 120 as the filter 100 is drawn into a catheter 140. Specifically, in the embodiment of FIG. 4, the catheter 140 is acting on the first portion 121 of the second set of legs 120, causing the first portion 121 to move into a position parallel with the axis of the filter 100. In some embodiments the barb 130, first portion 121 and second 124 portions of the legs 120, and the apex 127 of the legs may be configured such that, as the legs 120 are drawn into the catheter 140, the barb 130 tends to align with a portion of the legs 120, and moves into a position parallel to the axis of the filter 100. In such embodiments, the barbs 130 may be configured such that it does not interfere with the catheter 140 when the filter 100 is drawn into the catheter 140.

Similarly, the barb 130 associated with the first set 110 of legs may likewise be configured to align with the legs 110 as the legs are drawn into a catheter 140. In the embodiment of FIG. 4, the first set of legs 110 is sufficiently within the catheter 140 such that the barbs 130 associated with the first set of legs 110 are aligned with a portion of the first set of legs 110. Embodiments utilizing barbs 130 configured to align with a portion of the legs 110, 120 may include embodiments with bi-directional barbs. Moreover, barbs 130 configured to align with a portion of the legs 110, 120 may avoid the tendency of barbs 130 aligned opposite a catheter 140 from engaging the catheter 140 during retrieval.

In some embodiments, the filter 100 may be comprised of a shape memory alloy, for example nitinol. Thus, the filter 100 may be comprised of a material which, is first "set" in a particular shape when the filter 100 is being manufactured, then tends to return to that shape if it is subsequently deformed. The filter 100 may be "set" in the expanded configuration, or the shape generally shown in FIGS. 1-3. Drawing the filter 100 into a catheter 140, as shown in FIG. 4, may thus temporarily compress the legs 110, 120 within the catheter 140, though the filter 100 may be configured to return to the expanded shape upon deployment from the catheter 140. Thus, a filter may be configured with radially expanding legs which are elastically compressible into a position substantially parallel with the axis of the filter.

In some embodiments the filter 100 may be configured such that, when the filter 100 is deployed from a catheter 140, one set of legs 110, 120 engages the lumen walls before the other set of legs 110, 120.

Figure 5:
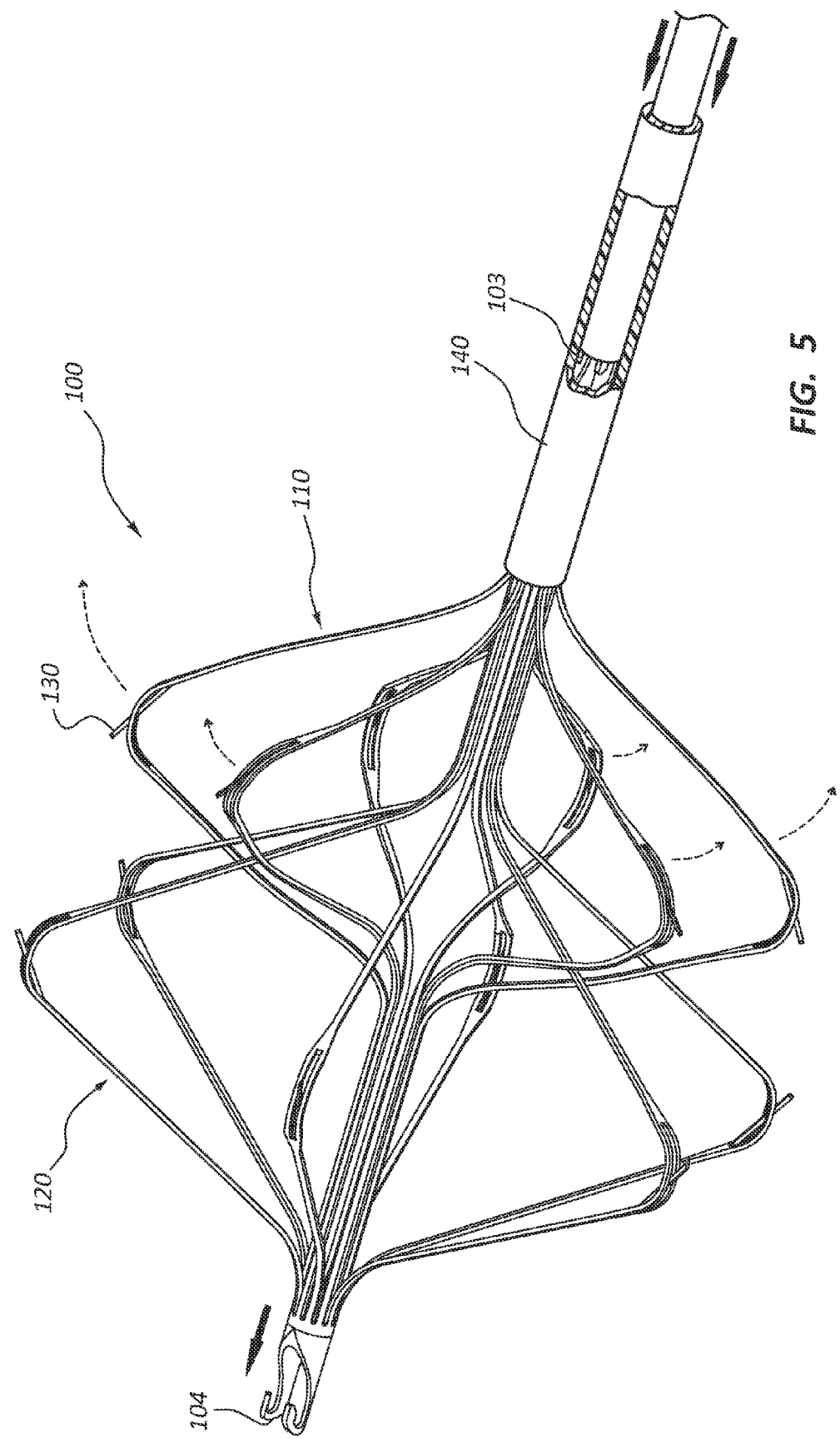
FIG. 5 is a perspective view of the filter of FIG. 1, partially disposed within the catheter of FIG. 4.

FIG. 5 is a perspective view of the filter 100 of FIG. 1, partially disposed within the catheter 140 of FIG. 4. As indicated by the arrows, in FIG. 5, the filter 100 is being deployed from the catheter 140. In some embodiments, the filter 100 may be configured to deploy such that one set of legs 110, 120 expands before the other set of legs 110, 120. For example, in FIG. 5, the second set of legs 120 is fully expanded, while the first set of legs 110 is still partially contained within the catheter 140. Thus, in the illustrated embodiment, the second set of legs 120 (and its associated barbs 130) may contact the wall of a body lumen prior to the first set of legs 110 when the filter 100 is deployed. Analogously, in some instances the filter may be oriented in the opposite direction within the catheter 140, with the first set of legs 110 exiting the catheter prior to the second set of legs 120 as the filter 100 is deployed. In such instances, the first set of legs 110 may contact the body lumen wall before the second set of legs 120.

Filters configured such that one set of legs 110, 120 contact the lumen wall prior to a second set of legs 110, 120 may stabilize the filter 100 during deployment. For instance, during deployment, interaction of the legs 110, 120 with the catheter 140 may tend introduce a biasing force between the filter 100 and the catheter 140. For example, in the embodiment of FIG. 5, the interaction of the first portion 121 of the second set of legs 120 and the catheter may tend to push the catheter 140 off the filter 100 as the legs 120 expand. Similarly, as the first set of legs 110 expands from the catheter 140 they may also exert a biasing force on the catheter 140. These biasing forces may make the filter 100 difficult to position during deployment as the biasing forces may cause the filter 100 to "jump" or erratically shift as it is deployed. However, in embodiments where one set of legs 110, 120 engage the lumen wall prior to the other set of legs 110, 120, contact between the legs 110, 120 and the lumen wall may stabilize the filter 100 and thus minimize the potential for improper placement of the filter 100 due to movement caused by biasing forces.

Figure 6:
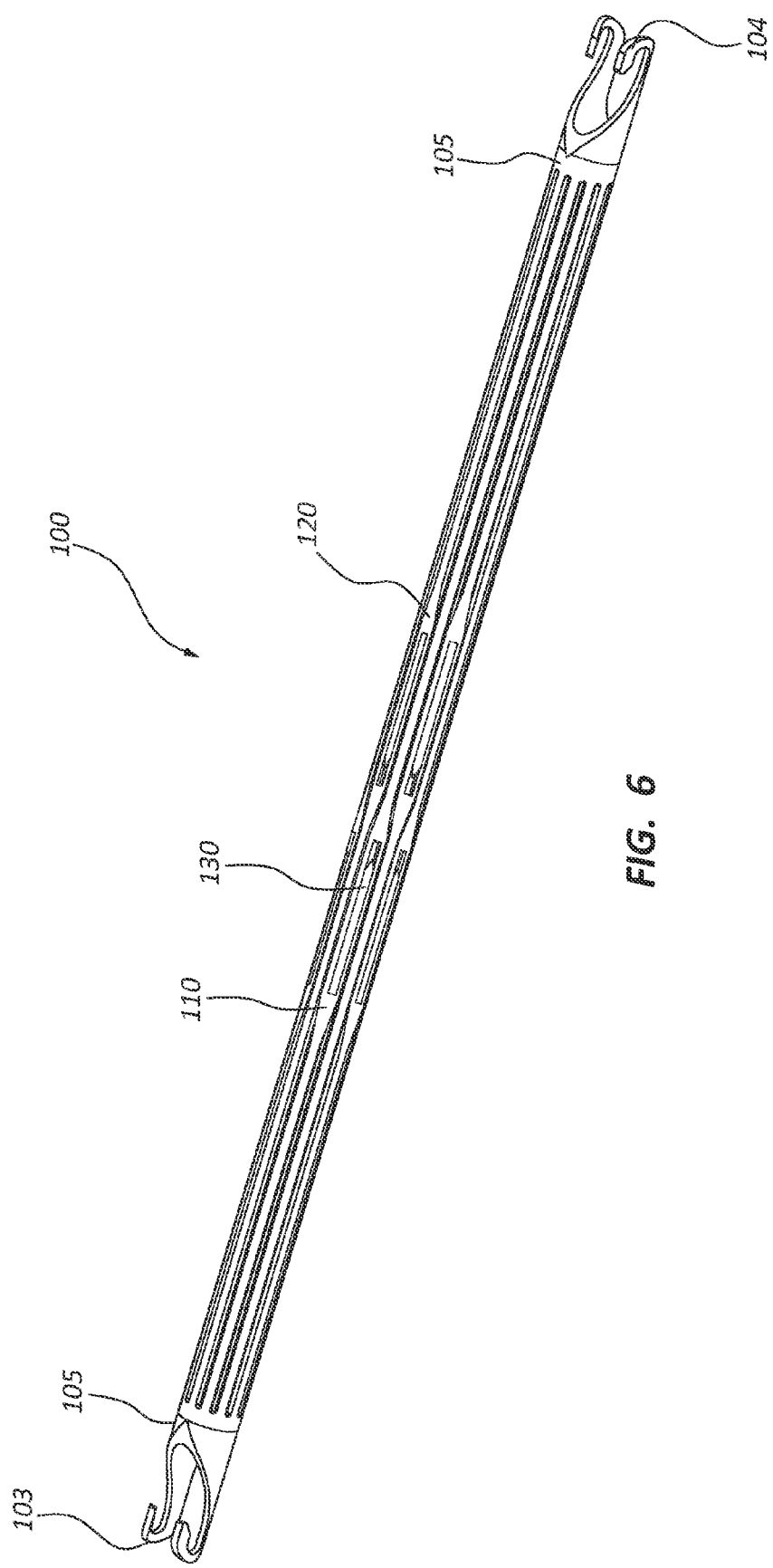
FIG. 6 is a perspective view of filter of FIG. 1 in a pre-expanded state.

FIG. 6 is a perspective view of filter 100 in a pre-expanded state. The filter 100 may be integrally formed from a single tube of material, for example, a tube of memory alloy. The shape of each component may first be cut, for example, by laser cutting, and any excess material subsequently removed. The components may then be formed, and set, into the desired shape of the filter. FIG. 6 illustrates the filter 100, formed from a single tube of material after the tube has been cut and the excess material removed, but before shaping. The tubular portion 105, the first set of legs 110, the second set of legs 120, and the barbs 130 all lie on the same cylinder—the tube from which they were formed—prior to shaping. FIG. 6 also illustrates the proximal 103 and distal 104 hooks of the filter 100.

Figure 7:
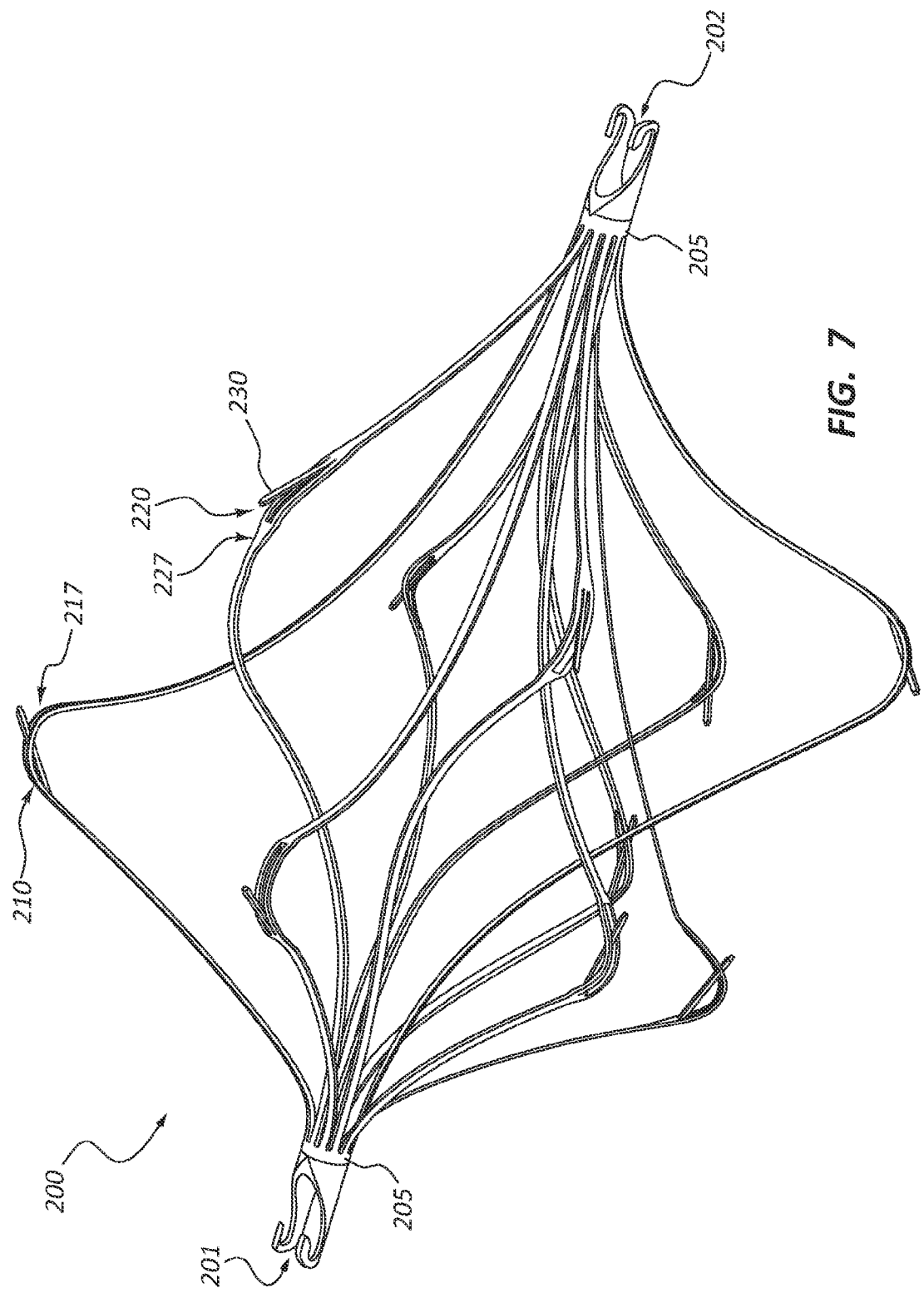
FIG. 7 is a perspective view of another embodiment of a filter.

FIG. 7 is a perspective view of another embodiment of a filter that can, in certain respects, resemble components of the filter described in connection with FIGS. 1-6. It will be appreciated that all the illustrated embodiments may have analogous features. Accordingly, like features are designated with like reference numerals, with the leading digits incremented to "2." (For instance, the filter is designated "100" in FIG. 1 and an analogous filter is designated as "200" in FIG. 7.) Relevant disclosure set forth above regarding similarly identified features thus may not be repeated hereafter. Moreover, specific features of the filter and related components shown in FIG. 7 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the filter of FIG. 7. Any suitable combination of the features, and variations of the same, described with respect to the filter and components illustrated in FIGS. 1-6, can be employed with the filter and components of FIG. 7, and vice versa. This pattern of disclosure applies equally to further embodiments depicted in subsequent figures and described hereafter.

The filter 200 of FIG. 7 comprises an axial member, such as the central tubular portion 205, coupled to a first set of legs 210 and a second set of legs 220. In the embodiment of FIG. 7, the filter 200 may define a hypothetical tubular surface extending between the tubular portions 205 adjacent the proximal 201 and distal 202 ends of the filter 200.

The filter 200 may comprise a first 210 and second 220 set of radially expanding legs which extend out from the tubular surface of the filter 200. In the illustrated embodiment, the legs of the first 210 and second 220 sets of legs are coupled to the axial member 205 adjacent the proximal 201 and distal 202 ends of the filter 200. Each leg of the first set of legs 210 may include an apex 217, displaced radially outward from the tubular surface and positioned between the proximal 201 and distal 202 ends of the filter 200. Similarly, each leg of the second set of legs 220 may define similar apexes 227. In some embodiments, barbs 230 may be coupled to some or all of the legs at the apexes 217, 227.

In some embodiments the filter 200 may be configured with bi-directional barbs, again, meaning barbs 230 positioned on different legs, which may be oriented in opposite directions. In the illustrated embodiment the barbs 230 associated with the first set of legs 210 are oriented in a different direction than the barbs associated with the second set of legs 220. In other embodiments, barbs 230 located on different legs of the same set of legs (210 and/or 220) may be oriented in opposing directions.

In contrast to the embodiment of FIGS. 1-6, it is noted that the filter 200 of FIG. 7 does not have portions of the legs 210, 220 disposed along the tubular surface of the filter 200. In other words, the filter 200 may not have transition portions such as portions 118 and 128 of filter 100. In other embodiments a filter may include transition portions.

In some embodiments, the filter 200 of FIG. 7 may be formed in a similar manner to the filter 100 of FIGS. 1-6, with the additional characteristic that the legs 210, 220 of the filter 200 travel around a portion of the circumference of the tubular surface as well as along the axial direction of the filter 200. In such embodiments, the legs 210, 220, may partially "twist" around the central axis of the filter 200. For example, in some embodiments the filter 200 may be substantially identical to the filter 100 of FIGS. 1-6, except that the proximal 201 and distal 202 ends are rotated (with respect to each other) about the central axis of the filter 200. Such twisting of the ends 201, 202 of the filter may result in the legs (which may be coupled to the axial member adjacent both the proximal 201 and distal 202 ends) following a twisting, or helical, path along the axial direction of the filter 200. In some embodiments, this rotation may be a permanent feature of the filter, meaning that the filter's natural shape (or the shape of the filter when unconstrained by external forces) includes this rotation of the proximal 201 and distal 202 ends and helically shaped legs 210, 220.

Figure 8:
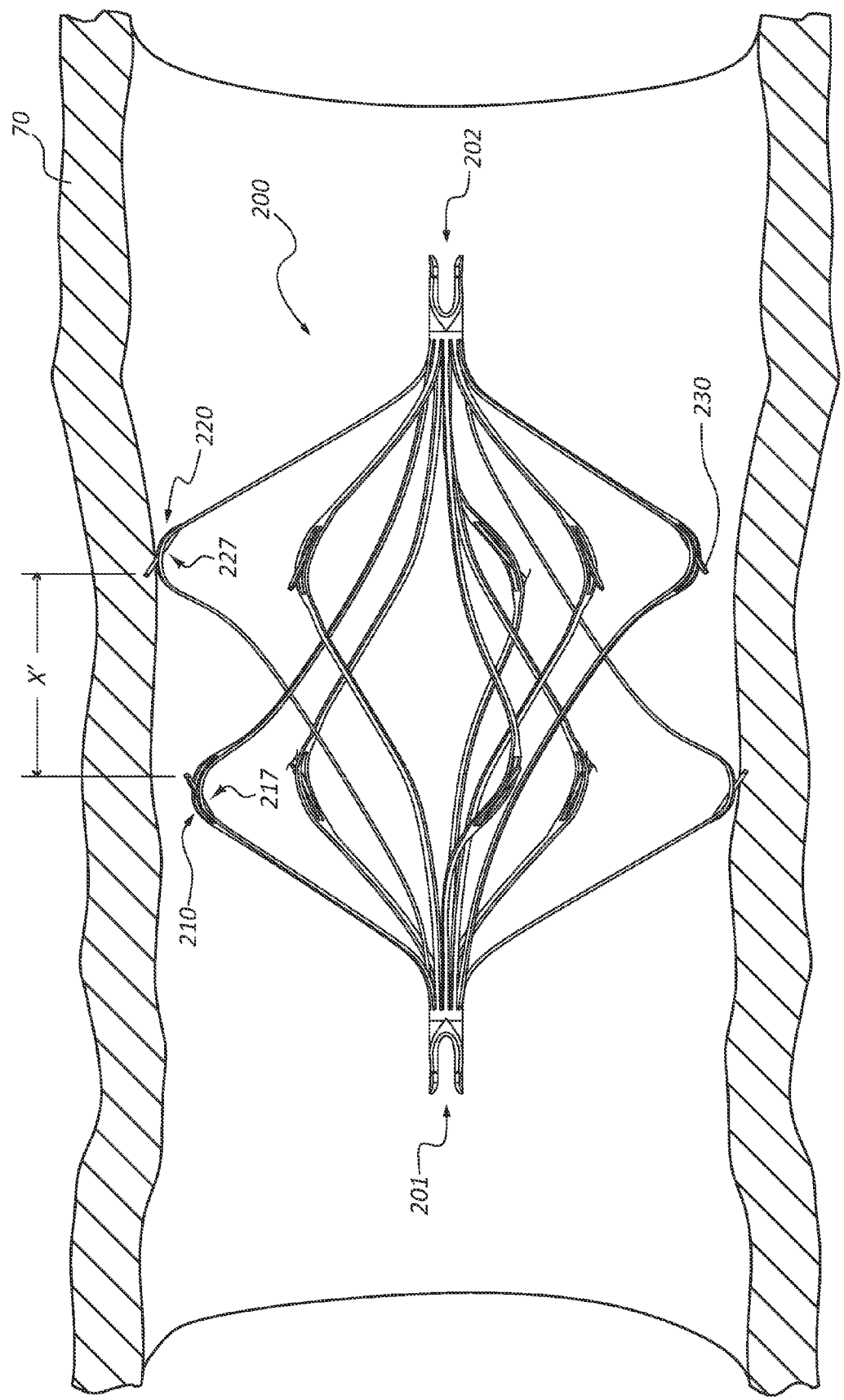
FIG. 8 is a side view of the filter of FIG. 7, disposed within a body lumen.

FIG. 8 is a side view of filter 200 disposed within a body lumen 70. Like the view of FIG. 2, in FIG. 8 the body lumen 70 is shown as a cross section, while the filter 200 is shown in perspective. This view illustrates how the rotation of the proximal 201 and distal 202 ends with respect to each other may offset portions of the same legs about the circumference of the filter 200.

The apexes 217, 227 of the first 210 and second 220 sets of legs may be displaced from each other a distance, such as distance X', along the longitudinal axis of the filter 200. In embodiments where the proximal 201 and distal 202 ends of the filter are twisted or rotated with respect to each other, the distance X' may or may not be constant around the circumference of the filter 200. Like distance X of filter 100, X' may be from about 0.200 inches to about 1.000 inches in some embodiments.

Figure 9:
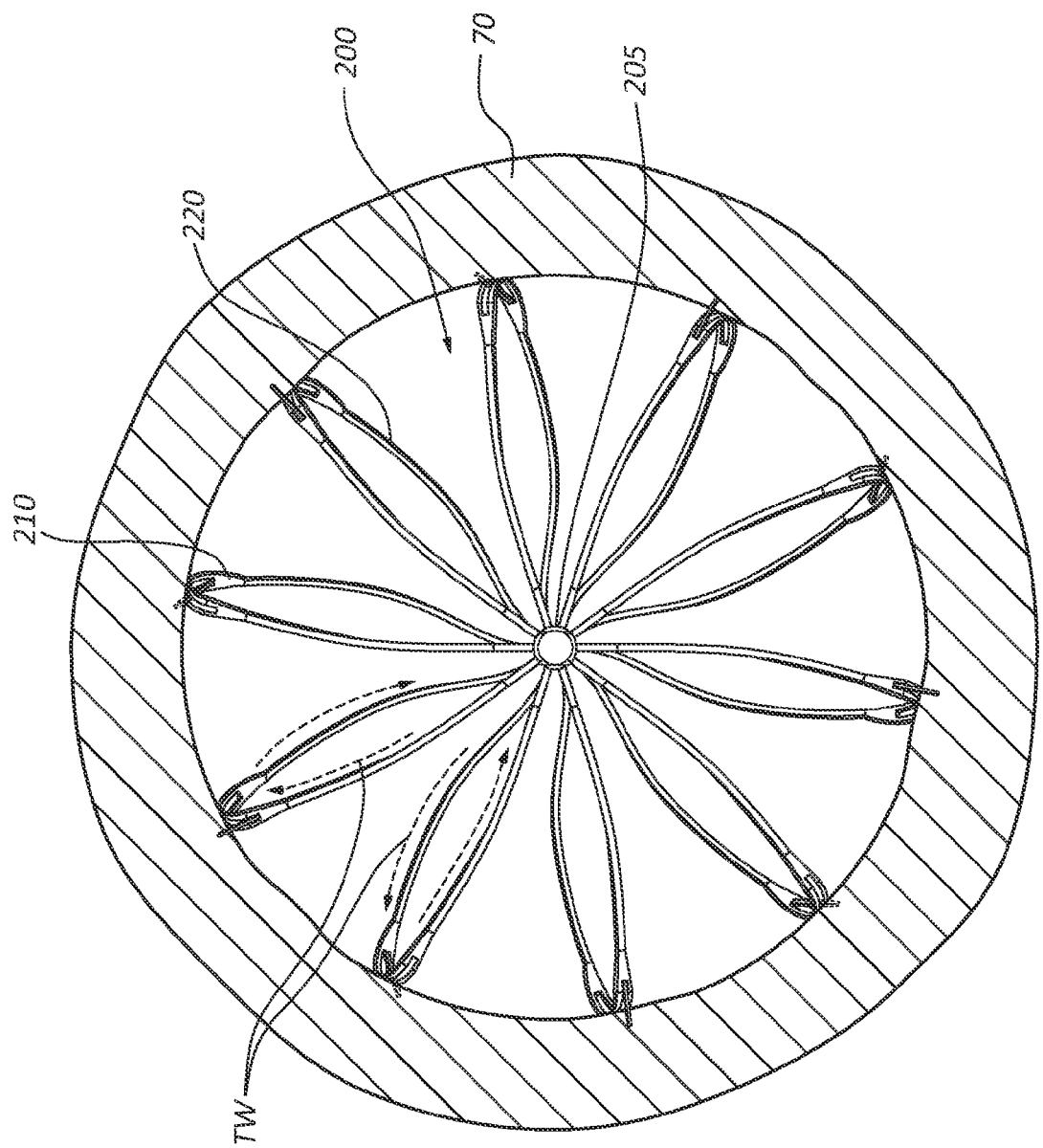
FIG. 9 is an end view of the filter of FIGS. 7 and 8, disposed within the body lumen of FIG. 8.

FIG. 9 is an end view of the filter of FIGS. 7 and 8, disposed within the body lumen of FIG. 8. FIG. 9 illustrates how the rotation of the proximal 201 and distal 202 ends may cause the legs of the filter to "twist" around a portion of the circumference of the filter as the legs 210, 220 run from one end of the filter 200 to the other. As shown by a comparison of FIGS. 9 and 3, this "twisting" may alter the end profile of the filter 200 as compared to filter 100. In some embodiments, the twisting or rotation of the ends 201, 202 may thus create a relatively more tortuous flow path through the filter 200, and may thereby provide desired filtering capabilities for certain applications.

The examples and embodiments disclosed herein are to be construed as merely illustrative and exemplary, and not a limitation of the scope of the present disclosure in any way. It will be apparent to those having skill in the art with the aid of the present disclosure that changes may be made to the details of the above-described embodiments without departing from the underlying principles of the disclosure herein. It is intended that the scope of the invention be defined by the claims appended hereto and their equivalents.

The invention claimed is:

1. A filter for a body lumen, comprising:
   an axial member having a first set of expandable legs and a second set of expandable legs,
   each leg of the first set of expandable legs comprising:
      a first portion, having an inner segment coupled to the axial member and an outer segment configured to be radially expandable from the axial member, wherein an external angle extending between an outside surface of the first portion and the axial member is an obtuse angle, and
      a second portion, having an outer segment coupled to the outer segment of the first portion and an inner segment coupled to the axial member, the outer segment of the second portion configured to be radially expandable from the axial member,
   wherein the first portion is coupled to the second portion at a first apex, wherein an internal angle extending between an inside surface of the first portion and an inside surface of the second portion is an acute angle, and wherein an external angle extending between an outside surface of the second portion and the axial member is an obtuse angle; and
   each leg of the second set of expandable legs comprising:
      a first portion, having an inner segment coupled to the axial member and an outer segment configured to be radially expandable from the axial member, wherein an external angle extending between an outside surface of the first portion and the axial member is an obtuse angle, and
      a second portion, having an outer segment coupled to the outer segment of the first portion and an inner segment coupled to the axial member, the outer segment of the second portion configured to be radially expandable from the axial member,
   wherein the first portion is coupled to the second portion at a second apex, wherein an internal angle extending between an inside surface of the first portion and an inside surface of the second portion is an acute angle, and wherein an external angle extending between an outside surface of the second portion and the axial member is an obtuse angle; and
   wherein the plurality of the first apexes of the first set of legs are spaced apart from the plurality of the second apexes of the second set of legs a distance parallel to a longitudinal axis of the axial member, when the first and second sets of legs are expanded.

2. The filter of claim 1, wherein the inner segments of the first and second portions of the first set of legs and the inner segments of the first and second portions of the second set of legs extend radially outward from the axial member when the legs are expanded.

3. The filter of claim 1, further comprising a plurality of barbs coupled to the first and second sets of expandable legs.

4. The filter of claim 3, wherein the plurality of barbs are coupled to the first and second sets of legs adjacent the first and second plurality of apexes.

5. The filter of claim 3, wherein the barbs associated with the first set of legs are oriented in a different direction than the barbs associated with the second set of legs.

6. The filter of claim 3, wherein the plurality of barbs are integrally formed with the first and second sets of legs.

7. The filter of claim 6, wherein the plurality of barbs are formed from center portions of the first and second sets of legs.

8. The filter of claim 3, wherein each barb is configured to align with a portion of the leg to which the barb is coupled, when the legs are drawn into a catheter.

9. The filter of claim 1, wherein the axial member comprises a tube.

10. The filter of claim 9, wherein the filter is integrally formed from the material of the tube.

11. The filter of claim 10, wherein the filter is cut from a tube of memory alloy.

12. The filter of claim 1, wherein the inner segments of the second portions of the first set of legs and of the second set of legs are coupled to the axial member by intermediate transition portions.

13. The filter of claim 12, wherein the transition portions are disposed substantially parallel to a central axis of the filter.

14. The filter of claim 12, wherein the transition portions are coupled to the axial member at a proximal or distal end of the filter.

15. The filter of claim 1, wherein the first set of legs is configured to engage a body lumen wall before the second set of legs when the filter is deployed.

16. The filter of claim 1, wherein the inner segments of the first portions of the first and second sets of legs are offset around a portion of a circumference of the filter from the inner segments of the second portions of the first and second sets of legs.

17. A filter for a body lumen, comprising:
an axial member integrally formed with, and having, a plurality of legs forming a first set of expandable legs and a plurality of legs forming a second set of expandable legs,
each leg of the first set of expandable legs comprising:
a first portion, having an inner segment coupled to the axial member and an outer segment configured to be radially expandable from the axial member, wherein an external angle extending between an outside surface of the first portion and the axial member is an obtuse angle, and
a second portion, having an outer segment coupled to the outer segment of the first portion and an inner segment coupled to the axial member, wherein an external angle extending between an outside surface of the second portion and the axial member is an obtuse angle, the outer segment of the second portion configured to be radially expandable from the axial member,
wherein the first portion is coupled to the second portion at a first apex, the first portion and the second portion both extending radially inward from the first apex at an acute angle relative to each other when the first set of legs are expanded; and
each leg of the second set of expandable legs comprising:
a first portion, having an inner segment coupled to the axial member and an outer segment configured to be radially expandable from the axial member, wherein an external angle extending between an outside surface of the first portion and the axial member is an obtuse angle, and
a second portion, having an outer segment coupled to the outer segment of the first portion and an inner segment coupled to the axial member, wherein an external angle extending between an outside surface of the second portion and the axial member is an obtuse angle, the outer segment of the second portion configured to be radially expandable from the axial member,
wherein the first portion is coupled to the second portion at a second apex, the first portion and the second portion both extending radially inward from the second apex at an acute angle relative to each other when the second set of legs are expanded; and
wherein the plurality of the first apexes of the first set of legs are spaced apart from the plurality of the second apexes of the second set of legs a distance parallel to a longitudinal axis of the axial member, when the first and second sets of legs are expanded.

18. The filter of claim 17, wherein,
each leg of the first set of expandable legs further comprises a transition portion disposed substantially parallel to the axial member, the transition member coupled to the inner segment of the second portion of each leg and to the axial member, and
each leg of the second set of expandable legs further comprises a transition portion disposed substantially parallel to the axial member, the transition member coupled to the inner segment of the second portion of each leg and to the axial member.

19. The filter of claim 17, wherein,
the plurality of the first portions of the first set of legs define a first radially expanding surface when the first set of legs is expanded,
the plurality of the second portions of the first set of legs define a second radially expanding surface when the first set of legs is expanded,
the plurality of the first portions of the second set of legs define a third radially expanding surface when the second set of legs is expanded, and
the plurality of the second portions of the second set of legs define a fourth radially expanding surface when the second set of legs is expanded.

20. The filter of claim 19, wherein one of the first and second radially expanding surfaces intersects one of the third and fourth radially expanding surfaces.

21. The filter of claim 19, wherein each surface is a frustoconical surface.

22. The filter of claim 17, wherein the filter is integrally formed from a tube of memory alloy.

23. The filter of claim 17, further comprising a plurality of barbs coupled to the first and second sets of expandable legs.

24. The filter of claim 23, wherein the plurality of barbs are formed from center portions of the first and second sets of legs.

25. The filter of claim 23, wherein the barbs associated with the first set of legs are oriented in a different direction than the barbs associated with the second set of legs.

26. The filter of claim 17, wherein the first set of legs is configured to engage a body lumen wall before the second set of legs when the filter is deployed.

27. The filter of claim 17, wherein the inner segments of the first portions of the first and second sets of legs are offset around a portion of a circumference of the filter from the inner segments of the second portions of the first and second sets of legs.

28. A filter for a body lumen, comprising:
a first set of expandable legs, each leg of the first set of legs having a first end and a second end;
a second set of expandable legs, each leg of the second set of legs having a first end and a second end; and
an axial member, wherein the first ends of the first and second sets of legs are coupled to the axial member adjacent a proximal end of the filter, wherein the second ends of the first and second sets of legs are coupled to the axial member adjacent a distal end of the filter, wherein each leg of the first and second sets of legs defines an obtuse external angle extending between an outside surface of the leg adjacent the first end of the leg and the axial member when the leg is expanded, and wherein each leg of the first and second sets of legs defines an obtuse external angle extending between an outside surface of the leg adjacent the second end of the leg and the axial member when the leg is expanded;
wherein the first ends of the first set of legs are circumferentially offset about a longitudinal axis of the filter from the second ends of the first set of legs and the first ends of the second set of legs are circumferentially offset about a longitudinal axis of the filter from the second ends of the second set of legs, wherein each leg of the first and second sets of legs defines an acute internal angle extending between inside surfaces of the leg adjacent the first and second ends of the leg when the leg is expanded.

29. The filter of claim 28, wherein each leg of the first and second sets of legs define an apex located between the first and second ends of the leg.

30. The filter of claim 29, wherein the apexes associated with the first set of legs are displaced from the apexes associated with the second set of legs a distance along an axial direction of the filter.

31. The filter of claim 29, further comprising a plurality of barbs each barb coupled to an apex.

32. The filter of claim 31, wherein the barbs associated with the first set of legs are oriented in a different direction than the barbs associated with the second set of legs.

33. The filter of claim 31, wherein each barb is configured to align with a portion of the leg to which the barb is coupled, when the legs are drawn into a catheter.

34. A medical device comprising a filter according to claim 1 disposed within a catheter.

35. A method of filtering clots or other matter in a body lumen, comprising:
obtaining the filter described in claim 1, and
disposing the filter within the body lumen of a patient.

36. The method of claim 35, wherein the filter is removably disposed within the body lumen.

37. The method of claim 35, wherein the body lumen is the vasculature.

38. The method of claim 35, wherein the body lumen is the inferior vena cava.

39. The method of claim 35, wherein the inner segments of the first portions of the first and second sets of legs are offset around a portion of a circumference of the filter from the inner segments of the second portions of the first and second sets of legs.

40. A method of deploying a filter, comprising:
inserting a filter into a body lumen, the filter comprising a first set of legs, each leg coupled to an axial member of the filter at a first and a second end of the leg, and a second set of legs, each leg coupled to the axial member at a first and a second end of the leg;
deploying a first set of legs of the filter, wherein each leg defines an acute internal angle extending between inside surfaces of the leg adjacent the first and second ends of the leg when the leg is deployed, wherein each leg defines an obtuse external angle extending between an outside surface of the leg adjacent the first end of the leg and the axial member when the leg is deployed, and wherein each leg defines an obtuse external angle extending between an outside surface of the leg adjacent the second end of the leg and the axial member when the leg is deployed;
contacting the body lumen with the first set of legs;
deploying a second set of legs of the filter, wherein each leg defines an acute internal angle extending between inside surfaces of the leg adjacent the first and second ends of the leg when the leg is deployed, wherein each leg defines an obtuse external angle extending between an outside surface of the leg adjacent the first end of the leg and the axial member when the leg is deployed, and wherein each leg defines an obtuse external angle extending between an outside surface of the leg adjacent the second end of the leg and the axial member when the leg is deployed;
stabilizing the filter by contact between the first set of legs and the body lumen while deploying the second set of legs; and
contacting the body lumen with the second set of legs after contacting the body lumen with the first set of legs.

41. The method of claim 40, wherein stabilizing the filter comprises minimizing shift of the filter while the second set of legs deploys.

42. The method of claim 40, wherein contact between the first set of legs and the body lumen partially opposes a biasing force between the second set of legs and a deployment device.

43. A filter for a body lumen, comprising:
an axial member comprising first and second ends and a longitudinal axis;
a plurality of legs, each of the plurality of legs comprising first and second ends, wherein the first end of each of the plurality of legs is attached to the first end of the axial member, and the second end of each of the plurality of legs is attached to the second end of the axial member;
wherein each of the plurality of legs compressibly extends radially from the axial member to an apex;
wherein at least two of the legs each define an acute internal angle extending between inside surfaces of each of the at least two legs adjacent the first and second ends of each of the at least two legs when each of the at least two legs is expanded;
wherein each of the at least two legs each define an obtuse external angle extending between outside surfaces of each of the at least two legs adjacent the first ends of each of the at least two legs and the axial member when each of the at least two legs is expanded;
wherein each of the at least two legs each define an obtuse external angle extending between outside surfaces of each of the at least two legs adjacent the second ends of each of the at least two legs and the axial member when each of the at least two legs is expanded; and
wherein at least two of the apexes are spaced longitudinally from one another.

44. The filter of claim 43, further comprising a barb extending from the apexes.

45. The filter of claim 43, wherein each of the plurality of legs comprises a sinusoidal curve.

46. The filter of claim 43, wherein each of the plurality of legs is elastically compressible to a position substantially parallel with a longitudinal axis of the axial member.

47. The filter of claim 43, wherein the first ends of the plurality of legs are offset from the second ends of the plurality of legs about a portion of a circumference of the filter.

* * * * *